(12) United States Patent
Freeman

(10) Patent No.: US 6,387,082 B1
(45) Date of Patent: *May 14, 2002

(54) OSTOMY APPLIANCE AND WOUND DRAINAGE DEVICE AND METHOD OF USING THE SAME

(75) Inventor: Frank Freeman, Abaco (BS)

(73) Assignee: E. R. Squibb & Sons, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/387,886

(22) Filed: Sep. 1, 1999

Related U.S. Application Data

(63) Continuation of application No. 08/507,592, filed on Jul. 26, 1995, now Pat. No. 5,951,533.

(51) Int. Cl.⁷ .................................................. A61F 5/44
(52) U.S. Cl. ........................ 604/338; 604/342; 604/604; 604/344
(58) Field of Search ............................... 604/342–344, 604/338, 339

(56) References Cited

U.S. PATENT DOCUMENTS 5,951,533 A  *  9/1999  Freeman ...................... 604/338

* cited by examiner

Primary Examiner—Kim M. Lewis
(74) Attorney, Agent, or Firm—Watov & Kipnes, PC

(57) ABSTRACT

An ostomy appliance or wound drainage device having a receptacle side component including a receptacle for receiving and storing waste solids and fluids and a bodyside component for adhering to the patient's skin around the stoma in which the two components are releasably sealed together through a pealable, washable based coupling mechanism.

28 Claims, 2 Drawing Sheets

OSTOMY APPLIANCE AND WOUND DRAINAGE DEVICE AND METHOD OF USING THE SAME

RELATED APPLICATION

This is a continuation-in-part application of U.S. patent application Ser. No. 08/507,592 filed Jul. 26, 1995 U.S. Pat. No. 5,951,533.

FIELD OF THE INVENTION

The present invention is directed to the field of ostomy appliances and wound drainage devices and particularly to an ostomy appliance and wound drainage devices having coupling members releasably secured to each other through a washable adhesive composition.

BACKGROUND OF THE INVENTION

Ostomy appliances and wound drainage devices hereinafter collectively referred to as ostomy appliances generally include a bag or pouch for collecting bodily wastes discharged from their surgically created stoma. The bag is connected to a pad or surgical dressing which is in contact with the patient's skin and surrounds the stoma.

Most ostomy appliances employ a coupling between the bag and the dressing which enables the bag to be readily removed when necessary, and replaced by a clean, empty bag. The coupling should provide a fluid tight seal to prevent leakage of liquids and/or gases.

Coupling systems are known in the art for reversibly securing the principal components of the ostomy appliance to each other. Such systems are disclosed, for example, in Peter L. Steer et al, U.S. Pat. Nos. 4,232,672; 4,460,363; and 4,518,389, Peter L. Steer, U.S. Pat. Nos. 4,636,205; 4,710,183; and 4,701,169, Keith T. Ferguson, U.S. Pat. No. 4,648,875 and Ronald Arnone et al, U.S. Pat. No. 4,642,107, each incorporated herein by reference.

Each of these systems relies on a mechanical coupling system to secure the ostomy bag to the dressing surrounding the stoma. Mechanical coupling devices, however, are prone to leakage because the contacting faces thereof eventually move out of face to face alignment. This occurs as a result of prolonged use of the device, changes in temperature and from manufacturing defects. It should also be noted that as the diameter of the mechanical coupling device increases, the security of the device generally decreases. Specifically, the larger diameter devices are more susceptible to being dislodged when the patient moves.

Ostomy appliances generally adhere to the patient's skin through the use of an adhesive. The adhesives are typically pressure sensitive and may contain additives which have soothing and/or healing properties to minimize patient discomfort during use of the ostomy appliance. For example, James L. Chen et al, U.S. Pat. No. 4,253,460, incorporated herein by reference, discloses an adhesive composition composed of a hydrocolloid gum, a pressure sensitive adhesive and a cohesive strengthening agent, optionally including pectin and gum karaya. Other examples of adhesive compositions for this use are disclosed in Arthur Doyle et al, U.S. Pat. No. 4,551,490 and John M. Pawelchak et al, U.S. Pat. No. 4,393,080, each incorporated herein by reference. Included among the disclosed adhesive compositions is a homogenous blend of mineral oil, at least one polyisobutylene alone or with an elastomer such as styrene radical or block type copolymers. The styrene copolymers include commercially available products sold by Shell Chemical Company under the tradename Kraton.

More recently an ostomy appliance has been sold under the trademark Microskin by Cymed, Inc. of Hayward, Calif. This device employs an adhesive to join facing surfaces of the respective coupling components. The coupling components are separated from each other by disrupting the adhesive seal and then attaching a new coupling device including a fresh ostomy bag. When the seal is broken the respective adhesive surfaces often have attached thereto particles of waste products that must be removed before a new ostomy bag can be added. After cleaning, respective surfaces must be substantially free of all contaminants to prevent infection.

Conventional adhesives such as employed in the Microskin product are disadvantageous. Although such adhesives may be washable, they have an adhesive quality in which the adhesive sticks to patient preferred cleaning implements employed by the patient to clean the coupling surfaces such as tissues, cloths and the like. The conventional adhesive compositions typically retain small particles of fibers from such cleaning implements and therefore cannot provide a contamination free surface for attachment of the next ostomy bag. In addition, such products employ a silicon release paper which is difficult to separate from the adhesive layer, especially for elderly patients.

In order to avoid this problem such prior devices require organic solvents to clean the coupling surfaces and must be dried without the convenience of using patient preferred cleaning implements.

Applicant has discovered that adhesive compositions can be employed to couple the principal components of an ostomy appliance together so as to eliminate the need for mechanical coupling devices. Such devices can provide a fluid tight seal that may be unsealed to replace the used ostomy bag with a new one and then resealed in fluid tight fashion. The problem of leakage of liquids and/or gases characteristic of ostomy appliances relying on mechanical seals can therefore be eliminated or at least minimized.

In addition, the present invention provides an adhesive coupling system that can provide a clean surface for the reapplication of a new ostomy bag using conventional cleaning implements.

SUMMARY OF THE INVENTION

The present invention is generally directed to ostomy appliances and wound drainage devices in which one part of the appliance containing the ostomy bag is adhesively coupled to a second part of the appliance which is attached to the patient around the stoma. The ostomy appliance of the present invention eliminates mechanical couplings and therefore provides greater security against the escape of liquids and/or gases. The adhesive coupling can be readily cleaned to provide at least a substantially contamination free surface for application of a new ostomy bag.

In particular, the present invention covers an ostomy appliance or wound drainage device comprising:

(a) an ostomy receptacle;

(b) a single pair of first and second coupling devices, said first coupling device having a first surface operatively engaged to the ostomy receptacle and an opposed surface for releasably engaging the second coupling device to form a releasable fluid tight seal therewith; and (c) said second coupling device having a first surface for operative contact with a patient's skin and an opposed surface for releasably coupling to the first coupling device at said opposed surface thereof, at least one of the respective opposed surfaces of the first and second coupling devices having thereon a washable adhesive composition capable of providing a releasable fluid tight seal substantially free of contamination when the first and second coupling devices are coupled to each other, said first and second coupling devices being releasable from each other while the second coupling device remains in operative contact with the patient's skin.

The adhesives chosen enable the first and second coupling devices to releasably adhere to one another. As a result the first and second coupling devices can be sealed, released and then resealed together. The coupling devices can therefore be disengaged and the ostomy receptacle replaced numerous times in a fluid tight sealing relationship to prevent leakage. The adhesives are preferably those which enable waste particles, bacteria and the like to be removed by conventional cleaning implements such as tissues and cloths without retention of fibers and other contaminants on the washed surface.

BRIEF DESCRIPTION OF THE DRAWINGS

The following drawings are illustrative of embodiments of the invention and are not intended to limit the invention as encompassed by the claims forming part of the application.

DETAILED DESCRIPTION OF THE INVENTION

The present invention is directed to an ostomy appliance and wound drainage device in which the principal components thereof are coupled together with an adhesive as opposed to mechanical coupling devices characteristic of the prior art. Coupling with an adhesive provides a fluid tight seal which can be peeled apart and then resealed when a replacement receptacle is desired. The present invention ensures substantially leak proof operation of the ostomy appliance during repeated use. The preferred adhesives are those that can be readily washed by conventional cleaning implements such as tissues, cloths and the like and still provide a substantially contamination free surface, especially free of fibers and the like.

Figure 1:
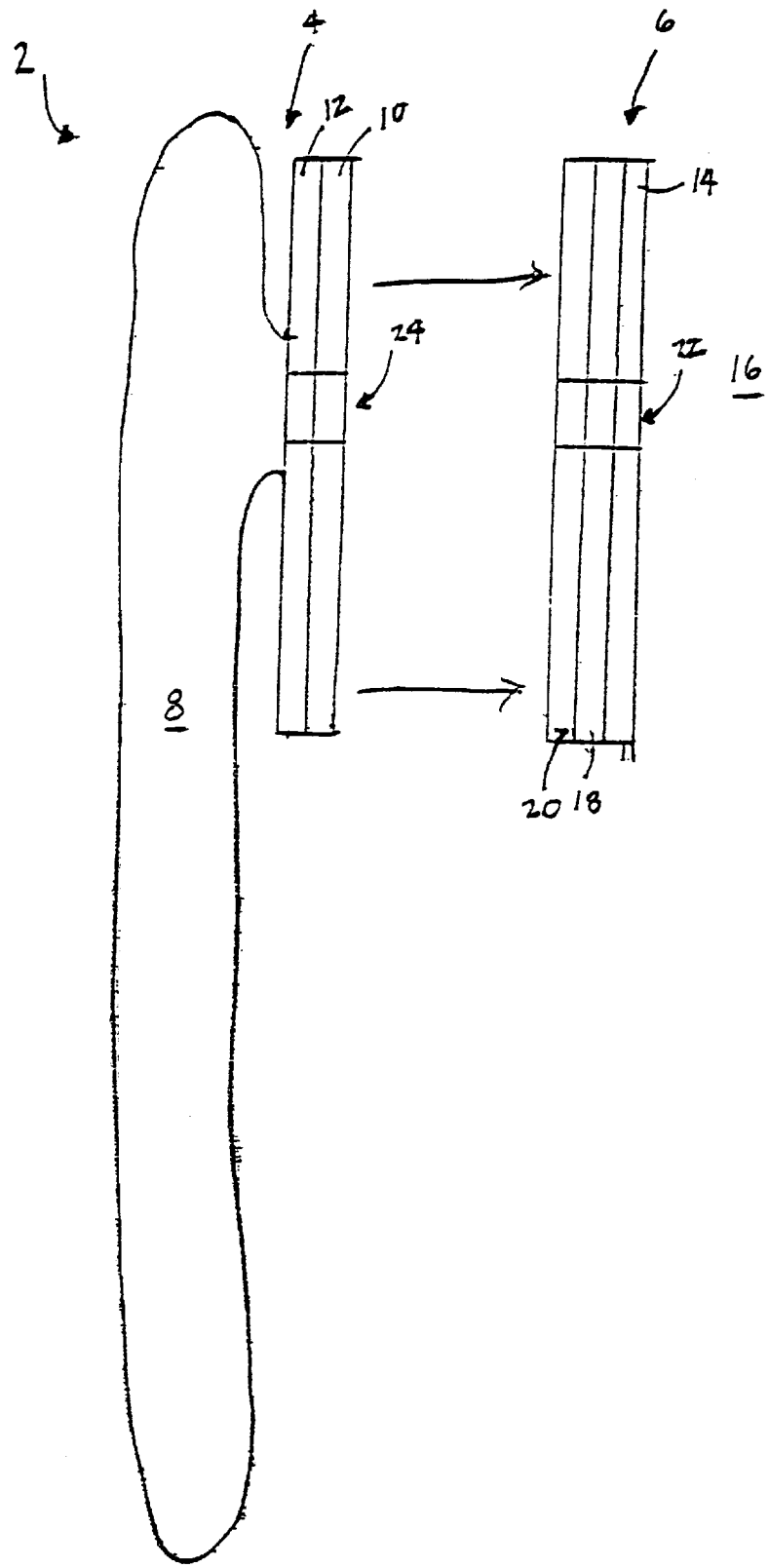
FIG. 1 is an exploded view of one embodiment of the ostomy appliance of the present invention.

Referring to the drawings and first to FIG. 1 there is shown an ostomy appliance 2 having two components capable of being coupled together in a fluid tight relationship The first of these components is a receptacle side component 4 and the second component is a bodyside component 6. The receptacle side component 4 includes a receptacle 8 for collecting discharged waste liquids and/or gases from the patient. As used herein the term "receptacle" shall include bags, pouches and the like which can be employed to collect waste fluids from an ostomy patient.

In accordance with the present invention, the receptacle side component 4 includes an adhesive layer 10 connected to the receptacle 8 through a substrate 12 which provides support for the adhesive layer 10. The substrate 12 can be made from any material which provides a surface for place-ment of the adhesive. Preferred substrates are webs or films, preferably having an irregular surface (e.g. naps) to insure anchoring of the adhesive 10 thereto. Examples of such substrates include non-woven fabrics made of polypropylenes, polyethylenes, polyesters, rayons and the like including blends thereof. Preferably the adhesive is impregnated with the substrate.

The adhesives which are used to form the adhesive layer 10 include thermoplastic elastomers such as styrene copolymers and acrylic adhesives. The preferred styrene copolymers include styrene-acrylonitrile-butadiene, styrene-butadiene-styrene, styrene-isoprene-styrene, styrene-ethylene/butylene-styrene and the like and blends thereof. Such copolymers of styrene are available, for example from Shell Chemical Company under the trademark Kraton. A preferred styrene copolymer is styrene-isoprene-styrene copolymer (e.g. Kraton D 1107 from Shell Chemical Company). Another preferred copolymer is styrene-acrylonitrile-butadiene having a relatively high butadiene content.

A preferred adhesive is one which may be washed and reused. Washable adhesives of this type include a gelled "Kraton" adhesive (e.g. Kraton D 1107) in which the styrene based polymer is gelled with an oil, preferably mineral oil. The amount of the styrene based polymer is preferably from about 70 to 90% by weight and the amount of the mineral oil is from about 10 to 30% by weight, based on the total weight of the styrene based polymer.

The adhesive composition of the type described above may be prepared, for example, by heating the mineral oil to a temperature of from about 120 to 150° C. and then adding the copolymer (e.g. Kraton D 1107) under stirring until the copolymer is dissolved. The resulting adhesive composition can be poured onto a suitable substrate or applied by a common hot melt applicator.

The most preferred types of adhesives are those which can be washed by conventional cleaning implements such as tissues and cloths without retaining fibers thereof and which form a fluid tight seal even after many applications. Such adhesives are disclosed, for example, in Homer C. Amos et al., U.S. Pat. No. 3,682,690, incorporated herein by reference.

In particular, the most preferred adhesive compositions are comprised of an elastomeric composition having a modulus of elasticity sufficient to enable waste particles to be readily removed therefrom with an internal viscosity low enough to enable water-washing and high enough to provide tack. Preferably the modulus of elasticity is in the range of from about 1 to 100 psi and the internal viscosity is from about 1000 to 20,000 poises. Preferred adhesive compositions are made of high molecular weight polyvinyl chloride or copolymers of vinyl chloride and vinyl acetate.

For water-washing applications as desired for the present ostomy appliance, the adhesive composition is hydrophobic wherein water will readily run off the surface, leaving the surface dry.

The softness of the tacky material used in the preferred adhesive composition can range from a modulus as low as 1, at which point the material is weak, to a modulus as high as 100. Values in the upper part of the range are satisfactory only with materials with a high "intrinsic adhesivity", i.e., a high surface free energy. In general, the softer, i.e., the lower the modulus, the greater the tack. Some materials, such as some polyvinyl chloride compositions, have a quite non-linear stress-strain curve. The first portion of the curve shows a very low modulus, but later the curve becomes very steep, indicating a very high modulus. In such materials, one can get the benefit of great softness with relatively high toughness.

Another requirement for washable tackiness which is particularly significant, is an internal viscosity between about 1,000 and 20,000 poises.

Most elastomers require a plasticizer to achieve a modulus as low as is desired. Materials such as neoprene and high-molecular-weight vinyls have little internal viscosity of their own, and the viscosity of the plasticized material is a fairly accurate reflection of the viscosity of the plasticizer itself. In any event, the internal viscosity must be low enough so that the material can quickly flow into large surface contact with the surface of the object to which tack is sought. But the viscosity must also be high enough so that he material does not yield too quickly to any force seeking to remove the object tacked onto the adhesive. Too low a viscosity results in little apparent tack. On the other hand, too high a viscosity results in the material feeling tacky with sustained contact pressure but not flowing quickly enough into large surface contact, with the contact surface, which involve very short-time contact pressure. Experience has shown that a viscosity in the neighborhood of 2500 to 5000 poises is most preferred. In general, viscosities outside the range of from 1000 to 20,000 poises give inferior results.

The internal viscosity can be measured by conventional means. In the case of highly plasticized vinyls or neoprene, measurement is unnecessary, for the plasticizer used therewith determines the resultant viscosity. The internal viscosity of materials such as polysulfides or polyurethanes which do not employ a plasticizer can be determined by comparing them with materials whose viscosity is known from its plasticizer.

A ball or the material in question is prepared, and a similar ball is prepared of the same modulus in a mixture of a high-molecular weight polyvinyl chloride, such as Geon 121 with a plasticizer whose internal viscosity is known. The surfaces are dusted with talc or a similar powder, and the rebounds are compared, the greater the rebound, the lower the viscosity. This method is crude but effective so long as care is taken to make the modulus, an easily measured property, of the two balls equal A better method is that further described in U.S. Pat. No. 3,682,690.

Tack is the result of a particular degree of softness and internal viscosity in combination with a property which might be termed the "intrinsic adhesivity", but which is better known as "surface free energy", the degree to which the Van der Waals forces within the material are bound. For example, in materials such as waxes or polytetrafluoroethylene, or (in general) materials composed of long unbranched chain molecules, the molecular bonds are tightly bound and show little of this quasi-chemical activity at the surface, and can be described as having a low intrinsic adhesivity. On the other hand, materials composed of short chain or highly branched molecules have many chain ends on any given surface, and thus have a high degree of quasi-chemical activity at the surface; these can be described as having a high intrinsic adhesivity. When compounding or choosing a washable tacky elastomer for a given application, the proper choice of characteristics as taught herein can be used to a great advantage. For instance, when extreme ease of washability is desired, a material such as a very high molecular weight polyvinyl chloride can be used as a base resin. This because of its low surface free energy and high elasticity will wash clean very easily, while the application of the principles taught herein regarding modulus and internal viscosity will give an aggressive tack even though the base resin has a low intrinsic adhesivity, by the addition of a suitable plasticizer.

If the plasticizer is used, it is important that it be highly compatible and not subject to excessive "sweating" It is preferred that the plasticizer be highly resistant to extraction by soapy water, since, otherwise, successive washings would soon destroy the efficacy of the material. The plasticizer should not be fugitive, i.e., it should have an extremely low vapor pressure, e.g., below $10^{-9}$ microns Hg. When used, the plasticizer imparts to the final product a desired value of internal viscosity and softness not inherent in those elastomers with which the plasticizer is used. If a copolymer of vinyl chloride and vinyl acetate is used, somewhat less plasticizer is preferred.

Almost any non-water-soluble elastomer will give satisfactory results if formulated in the manner described herein. The high-molecular weight vinyl chloride plastics have the advantages of low cost, ease of handling, transparency, low surface free energy, and a non-linear stress-strain curve lends toughness.

The adhesive composition may also include in addition to tackifiers, antioxidants, antibiotics, antimicrobial agents and the like in effective amounts known to those of ordinary skill in the art.

The bodyside component 6 of the ostomy appliance 2 includes a bodyside adhesive layer 14 which is adapted to adhere to the patient's skin and is shown generally by the numeral 16. Adhesive compositions which can be used to adhere the ostomy appliance 2 to the patient are known and include those previously mentioned in connection with U.S. Pat. Nos. 4,253,460; 4,393,080; and 4,551,490.

As shown in the embodiment of FIG. 1, the bodyside component 6 is further provided with a substrate 18 and an adhesive layer 20 which correspond in structure and function to the substrate 12 and adhesive layer 10, respectively of the receptacle side component 4. The substrate 18 is preferably a web or film made from non-woven fabrics including polypropylenes, polyethylenes, polyesters, rayons and the like and blends thereof. The web or film preferably has a nap or irregular surface which facilitates the anchoring of the adhesive thereto. The adhesive layer 20 is preferably made of the adhesives described above and in particular those mentioned in U.S. Pat. No. 3,682,690. The adhesive employed for the adhesive layer 20 is preferably washable and reusable so that the receptacle side component 4 and the bodyside component 6 may be peeled away from each other and a new receptacle inserted into the ostomy appliance with a substantially contamination free coupling.

In operation, the bodyside component 6 of the ostomy appliance 2 is adhered to the patient's skin 16 by the adhesive layer 14 so that a passageway 22 therein is aligned with the stoma (not shown) created by the surgical procedure. The receptacle side component 4 having a similar passageway 24 is then placed into contact with the bodyside component 6 through the respective adhesive layers 10,20 so that the respective passageways 22,24 are aligned thereby enabling waste liquids and gases escaping from the stoma to proceed into the receptacle 8. When the receptacle 8 is filled with waste fluids or solids and must be replaced, the adhesive layer 10 is peeled away from the adhesive layer 20 thereby separating the receptacle side component 4 from the bodyside component 6 while the latter remains attached to the patient's skin. Alternatively, the ostomy appliance may be removed from the patient's skin and then the components 4,6 peeled away from each other. Once separated, the adhesive layer 20 is washed, preferably in a manner most suitable to the patient such as being water washing with tissues, cloth and the like. Washing provides a substantial contamination free surface which is free of fibers and the like. The components 4, 6 are then reattached to adhesively reseal a new receptacle side component 4 through its adhesive layer 10. The ostomy appliance 2 is then ready for continued operation.

It should be understood that the disengagement of the components 4,6 can be made at any time during operation of the ostomy appliance. For example, if an adjustment of the ostomy appliance 2 on the patient's skin is necessary, the receptacle side component 4 may first be peeled away from the bodyside component 6 as explained previously. The bodyside component may then be removed and repositioned about the stoma followed by the resealing of the components 4,6 through the respective adhesive layers 10,20.

Figure 2A:
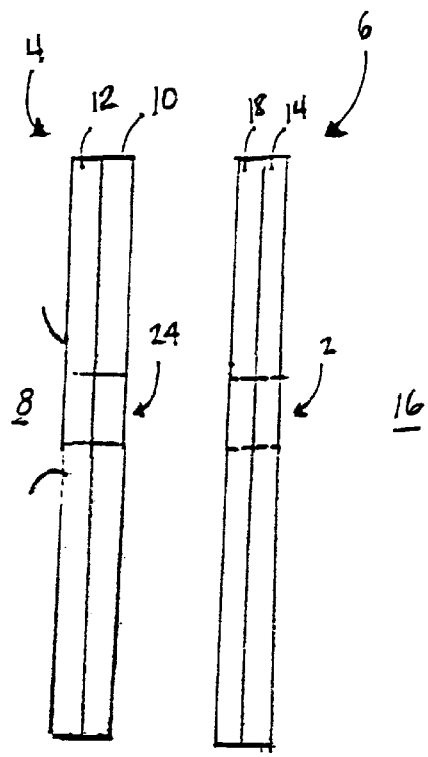
FIG. 2A is a side view of another embodiment of the invention with an adhesive on the receptacle side component only.
Figure 2B:
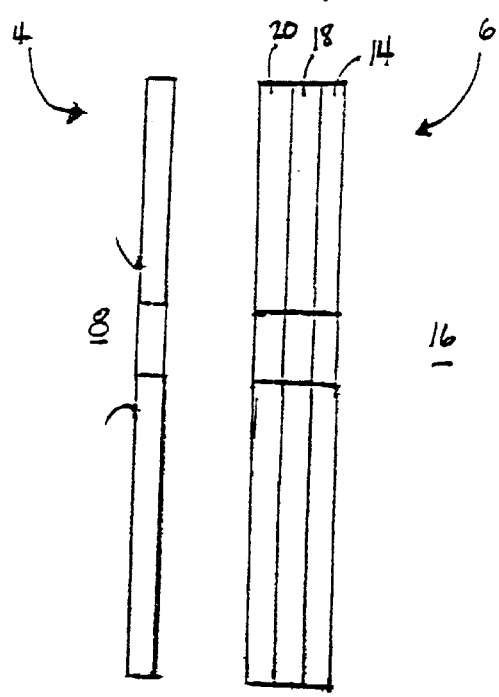
FIG. 2B is a side view of a further embodiment of the invention with an adhesive on the bodyside component only.

Although preferred particularly when using the preferred adhesive composition, it is not essential that both the receptacle side component 4 and bodyside component 6 have an adhesive layer. As shown in FIGS. 2A and 2B, only one of the components 4,6 has an adhesive layer. More specifically, FIG. 2A shows an embodiment of the ostomy appliance of the present invention wherein the receptacle side component 4 has an adhesive layer 10 but the bodyside component 6 has been constructed without a corresponding adhesive layer.

The operation of the ostomy appliance shown in FIG. 2A is essentially the same as that described above for the embodiment of FIG. 1. The bodyside component 6 is adhered to the patient's skin and either before of after the procedure, the components 4,6 are placed into contact wherein the adhesive layer 10 sealingly engages the substrate 18 of the bodyside component 6.

In a further embodiment of the invention as shown in FIG. 2B, the bodyside component 6 is provided with an adhesive layer 20 but the receptacle side component is not provided with a corresponding adhesive layer. The components 4,6 are placed in operative contact in the same manner as described above for the embodiment of FIG. 2B.

As shown in the embodiments described above, the ostomy appliance of the present invention employs a resealable adhesive based coupling mechanism that provides a fluid tight seal and provides significant advantages over mechanical coupling mechanisms that are prone to leakage particularly when subjected to repeated use. In addition, adhesive compositions employed in the present invention provide a surface which can be readily cleaned by conventional cleaning implements without leaving residual fiber materials thereon.

EXAMPLE 1

| Ingredient: | Parts by weight |
|---|---|
| High-molecular-weight polyvinyl chloride, e.g., Geon 121 made by B. F. Goodrich | 100 |
| Plasticizer, a polyester condensation product of sebacic acid and ethylene glycol of approximately 8000 molecular weight, e.g., Paraplex G25 made by Rohm and Haas | 400 |
| Barium zinc phenate, e.g., Argus Chemical Co., Mark KCB | 4 |

Suitable pigment or dye, if desired, may be added. The suggested cure cycle is 10 min. at 380° F.

This composition has an internal viscosity of 2200 poises, a Young's modulus of about 10 p.s.i., and a permanent tack angle of 3°.

Similar results may be obtained by substituting a copolymer of polyvinyl chloride and polyvinyl acetate for the polyvinyl chloride, the copolymer preferably having approximately the same physical qualities as that of this example and usually requiring slightly less plasticizer.

EXAMPLE 2

| Ingredient: | Parts by weight |
|---|---|
| High-molecular-weight polyvinyl chloride, e.g., Geon 121 made by B. F. Goodrich | 100 |
| Plasticizer, a polyester condensation product of sebacic acid and ethylene glycol of approximately 8000 molecular weight, e.g., Paraplex G25 made by Rohm and Haas | 400 |
| A glycerol ester of hydrogenated rosin, e.g., Staybelite Ester 10 made by Hercules, Inc. | 100 |
| Barium zinc phenate, e.g., Argus Chemical Co., Mark KCB | 4 |

Suitable pigment or dye, if desired, may be added. The suggested cure cycle is 10 min. at 380° F.

This composition has an internal viscosity of about 8 minutes (e.g. about 6,000 poises), a Young's modulus of about 10 p.s.i., and a permanent tack angle of about 3°.

EXAMPLE 3

The procedure of Example 1 is repeated except that 20% of the Geon 121 polyvinyl chloride is replaced by Geon 222, a very short chain polyvinyl chloride copolymer of high intrinsic adhesivity. The resulting composition has a tack similar to Example 1 but a higher intrinsic adhesivity or surface free energy.

EXAMPLE 4

The procedure of Example 1 is repeated except that 100 parts by weight of butyl benzyl phthalate is added. The resulting composition has an internal viscosity of about 1000 poises with reduced tack and modulus.

EXAMPLE 5

| Ingredient: | Parts by weight |
|---|---|
| Component A | |
| Polyether triol, e.g., Wyandotte TP 4542 | 100 |
| Toluene di-isocyanate, e.g., Allied Chemical Nacconate | 12 |
| The mixture is held at 160° F. for 4 hours. | |
| Component B | |
| Polyether triol as in Component A | 100 |
| Tin octoate catalyst, e.g., Witco Chemical Co. tin catalyst C-4 | 0.5 |
| The two prepared components are mixed in the proportions, by weight of | |
| Component A | 100 |
| Component B | 83 |

Cure 4 hours at 180° F.

EXAMPLE 6

| | Parts by weight |
|---|---|
| (A) Resin component | |
| Polyalkylene polysulfide, e.g., Thiokol LP 31 | 100 |
| Chlorinated biphenyl, e.g., Monsanto Arcoclor 1254 | 90 |
| Calcium carbonate, e.g., Diamond Alkali Co. Super Multifex | 30 |
| Liquid coumarin-indene alkylated phenol, e.g., Neville Chemical Co. 10° Nevillac | 20 |
| Bis-phenol-A and epichlorhydrin epoxy resin, e.g., Shell Chemical Epon 836 | 3 |
| Stearic acid | 0.5 |
| Sulfur | 0.1 |
| (B) Catalyst component | |
| Lead oxide | 100 |
| Chlorinated biphenyl, e.g., Monsanto Aroclor 1254 | 30 |
| Xylene | 10 |
| Zinc stearate | 2.5 |
| Stearic acid | 1.5 |

Then two components are mixed in the preferred ratio of one hundred parts by weight of the resin mix to three and one-half parts of catalyst mix and cured at 160° F. for two hours.

EXAMPLE 7

| | Parts by weight |
|---|---|
| Rubber solution: | |
| Polychloroprene, e.g., DuPont Neoprene W | 100 |
| Toluene | 240 |
| Methyl ethyl ketone | 160 |
| The mixture is stirred or tumbled until the neoprene is dissolved. | |
| Premix of catalyst, plasticizers, etc. | |
| Chlorinated biphenyl, e.g., Monsanto Aroclor 1254 | 20 |
| Zinc oxide | 10 |
| Magnesium oxide | 5 |
| Phenyl-beta-naphthylamine, e.g., DuPont Neozone D | 4 2 |
| Ethyl thiourea, e.g., DuPont Accelerator NA22 | 1 |
| The materials are dispersed in the Aroclor, and then the following materials are added and mixed: | |
| Monsanto Aroclor 1254 | 55 |
| Neville Chem. Co. 10° Nevillac | 25 |

The premix is added to the rubber solution and mixed. After it is thoroughly dry, cure for 30 minutes at 250° F.

Whatever the composition, it is preferable that the thickness of the adhesive composition be from about 0.003 to 0.017 inch, preferably about 0.010 inch to 0.005 inch, for most applications.

What is claimed is:

1. An ostomy appliance or wound drainage device comprising:
   (a) a receptacle;
   (b) a single pair of first and second coupling devices, said first coupling device having a first surface operatively engaged to the receptacle and an opposed surface for releasably engaging the second coupling device to form a releasable fluid tight seal therewith; and
   (c) said second coupling device having a first surface for operative contact with a patient's skin and an opposed surface for releasably coupling to the first coupling device at said opposed surface thereof, at least one of the respective opposed surfaces of said first and second coupling devices having thereon a washable adhesive composition capable of providing a releasable fluid tight seal substantially free of contaminants when the first and second coupling devices are coupled to each other, said first and second coupling devices being releasable from each other while the second coupling device remains in operative contact with the patient's skin.

2. The appliance or device of claim 1 wherein the respective opposed surfaces of the first and second coupling devices each have thereon said adhesive composition, said first and second coupling devices being releasable and resealable when operatively engaged and then disengaged from each other.

3. The appliance or device of claim 1 wherein the adhesive composition is at least one thermoplastic elastomer.

4. The appliance or device of claim 3 wherein the thermoplastic elastomer is a styrene copolymer or an acrylic resin.

5. The appliance or device of claim 4 wherein the styrene copolymer is selected from the group consisting of styrene-acrylonitrile-butadiene, styrene-butadiene-styrene, styrene-isoprene-styrene and styrene-ethylene/butylene-styrene.

6. The appliance or device of claim 5 wherein the styrene copolymer is a styrene-isoprene-styrene copolymer or a styrene-acrylonitrile-butadiene copolymer having a relatively high butadiene content.

7. The appliance or device of claim 5 wherein the styrene copolymer is combined with an oil to form a gel.

8. The appliance or device of claim 1 wherein the adhesive composition comprises an elastomeric composition having a modulus of elasticity sufficient to enable waste particles to be readily removed therefrom, and having an internal viscosity low enough to enable water-washing and high enough to provide tack.

9. The appliance or device of claim 8 wherein the modulus of elasticity is from about 1 to 100 psi and the internal viscosity is from about 1000 to 20,000 poises.

10. The appliance or device of claim 9 wherein the adhesive composition further comprises a plasticizer.

11. The appliance or device of claim 9 wherein the adhesive composition is solid, hydrophobic and insoluble in water.

12. The appliance or device of claim 9 wherein the adhesive composition comprises high molecular weight polyvinyl chloride.

13. The appliance or device of claim 9 wherein the adhesive composition comprises a copolymer or vinyl chloride and vinyl acetate.

14. The appliance or device of claim 1 wherein each of the first and second coupling devices further comprise a substrate, said adhesive composition being placed on at least one of said substrates.

15. The appliance or device of claim 14 wherein the substrate has an irregular surface to facilitate anchoring of the adhesive composition.

16. The appliance or device of claim 15 wherein the film or web is made of a non-woven fabric.

17. The appliance or device of claim 16 wherein the non-woven fabric is made of a material selected from the group consisting of polypropylene, polyethylene, polyester, rayon and blends thereof.

18. The appliance or device of claim 14 wherein the substrate is comprised of a film or web.

19. A method of collecting fluid or solid waste from a patient using an ostomy appliance or wound drainage device comprising:
 a) placing a bodyside coupling device having a first surface in contact with the patient's skin, said bodyside coupling device having an opposed surface; and
 b) reversibly engaging a receptacle side coupling device to the bodyside coupling device through a washable adhesive composition at said opposed surface thereof to provide a passageway for the flow of said fluid into a receptacle attached to the receptacle side coupling device.

20. The method of claim 19 wherein the adhesive composition is at least one thermoplastic polymer.

21. The method of claim 20 wherein the thermoplastic elastomer is a styrene copolymer or an acrylic resin.

22. The method of claim 21 wherein the styrene copolymer is selected from the group consisting of styrene-acrylonitrile-styrene, styrene-butadiene-styrene, styrene-isoprene-styrene and styrene-ethylene/butylene-styrene.

23. The method of claim 19 wherein the adhesive composition has a modulus of elasticity sufficient to enable waste particles therefrom and having an internal viscosity low enough to enable water-washing and high enough to provide tack.

24. The method of claim 23 wherein the modulus of elasticity is from about 1 to 100 psi and the internal viscosity is from about 1000 to 20,000 poises.

25. The method of claim 19 wherein the adhesive composition further comprises a plasticizer.

26. The method of claim 19 wherein the adhesive composition is solid, hydrophobic and insoluble in water.

27. The method of claim 19 wherein the adhesive composition comprises high molecular weight polyvinyl chloride.

28. The method of claim 19 wherein the adhesive composition comprises a copolymer of vinyl chloride and vinyl acetate.

* * * * *